United States Patent [19]

Grow et al.

[11] Patent Number: 5,094,956
[45] Date of Patent: Mar. 10, 1992

[54] FECAL SAMPLE IMMUNOASSAY COMPOSITION AND METHOD

[75] Inventors: Michael A. Grow, San Jose; Vipin D. Shah, Saratoga, both of Calif.

[73] Assignee: International Immunoassay Laboratories, Inc., Santa Clara, Calif.

[21] Appl. No.: 329,455

[22] Filed: Mar. 28, 1989

Related U.S. Application Data

[63] Continuation-in-part of Ser. No. 10,787, Feb. 4, 1987, abandoned.

[51] Int. Cl.⁵ ............................................. G01N 33/72
[52] U.S. Cl. ..................................... 436/66; 436/8; 436/17; 436/63; 436/177; 436/815; 436/825; 435/184
[58] Field of Search ............... 436/518, 525, 530, 531, 436/63, 66, 177, 815, 824, 825; 435/7, 184

[56] References Cited

U.S. PATENT DOCUMENTS

| | | | |
|---|---|---|---|
| 3,869,547 | 3/1975 | Mebus et al. | 424/89 |
| 4,200,690 | 4/1980 | Root et al. | 435/7 |
| 4,424,279 | 1/1984 | Bohn et al. | 435/7 X |
| 4,533,630 | 8/1985 | Wilkins et al. | 435/7 |
| 4,683,197 | 7/1987 | Gallati | 435/7 |
| 4,920,045 | 4/1990 | Okuda et al. | 436/66 |

FOREIGN PATENT DOCUMENTS

| | | |
|---|---|---|
| 0030388 | 9/1980 | European Pat. Off. |
| 0032782 | 1/1981 | European Pat. Off. |
| 0111916 | 12/1983 | European Pat. Off. |
| 0175326 | 9/1985 | European Pat. Off. |

OTHER PUBLICATIONS

Clinical Diagnosis and Management by Laboratory Methods, vol. II, Henry, J. B. (ed)., W. B. Saunders Company, Philadelphia, pp. 1735-1736 (1974).
Textbook of Clinical Chemistry, Tietz, N. W. (ed.), W. B. Saunders Company, Philadelphia, p. 492 (1986).
Klein-(immuology, The Science of Self-Nonself Discrimination (1982) Wiley Sons, New York, N.Y., pp. 23, 158 & 516.
Julkunen et al., Scandinavian Journal of Infectious Diseases 17:245-249 (1985).
Textbook of Clinical Chemistry, Tietz, N. W. (ed.), W. B. Saunders Company, Philadelphia, p. 1562 (1986).
Harrison's Principles of Internal Medicine, Braunwald, E. et al., (ed.), McGraw-Hill Book Company, New York, pp. 707-708 (1987).

Primary Examiner—Sam Rosen
Attorney, Agent, or Firm—Skjerven, Morrill, MacPherson, Franklin & Friel

[57] ABSTRACT

A method for preparing a fecal sample of immunoassay testing comprising the steps of dispersing a sample of from 1 to less than 10 wt. % of a stool sample in an aqueous fecal test solution formulated with one or more preservatives, analyte stabilizing agents and endogenous interference reducing agents. The fecal solids are then permitted to settle to form a liquid phase substantially free from fecal solids, and the clarified liquid phase is removed to provide a test sample free from fecal solids. The fecal test solutions contain suitable stool stabilizers such as buffers and antimicrobial agents, analyte protecting agents such as proteolytic, reductive or oxidative enzyme inhibitors, endogenous assay interfering enzyme inhibitors such as a reducing agent, and non-specific binding inhibitors such as animal proteins. The stool sample should be fresh or be fresh frozen and thawed immediately before dispersion in the buffer solution. The sample is suitable for any solid-phase immunoassay determination of a fecal sample analyte. A method for determining analyte in a stool sample comprises conjugating anti-analyte antibody adhered to a insoluble support with analyte in the clarified sample, and determining the presence and extent of such conjugation. For determining human hemoglobin in a sample of human stool, the aqueous fecal test solution preferably contains a proteinase inhibitor, formaldehyde and an animal albumin.

8 Claims, 1 Drawing Sheet

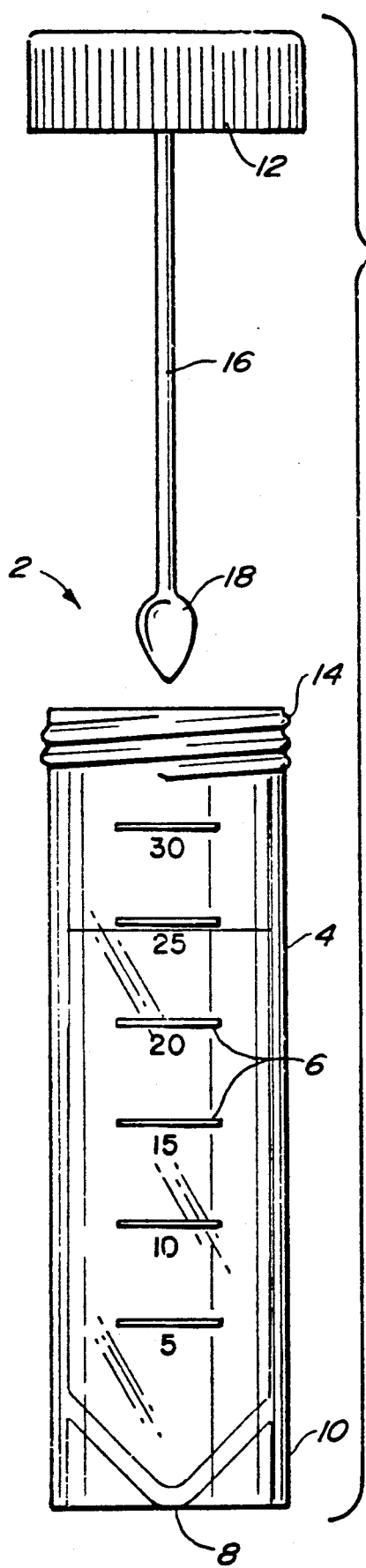
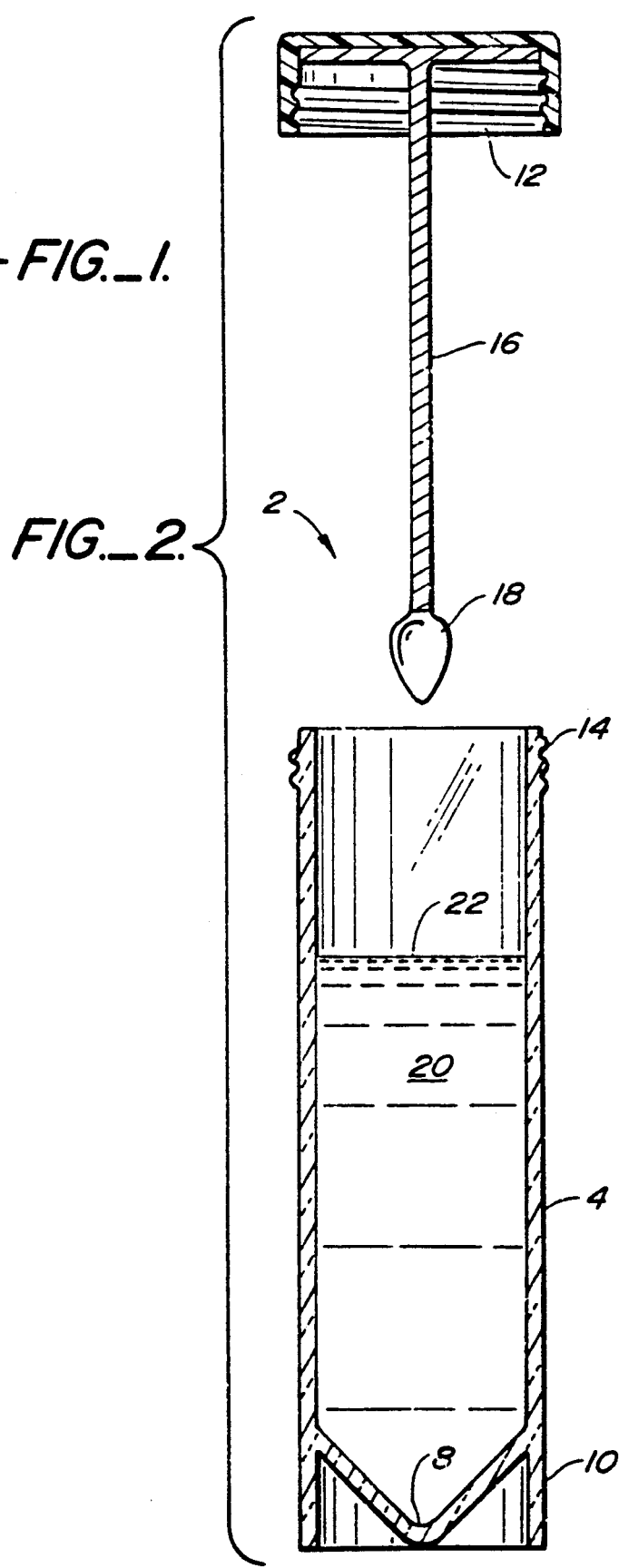

FECAL SAMPLE IMMUNOASSAY COMPOSITION AND METHOD

CROSS REFERENCE TO RELATED APPLICATION

The present application is a Continuation-In-Part application of U.S. application Ser. No. 07/010,787 filed Feb. 4, 1987, now abandoned entitled Fecal Sample Immunoassay Composition and Method by Grow et al, which application is incorporated herein by reference in its entirety.

FIELD OF THE INVENTION

This invention relates to an improved method for analyzing fecal samples. In particular, this invention relates to a method for preparing fecal samples for immunoassays, the prepared fecal sample compositions and to solid-phase immunoassays for determining the presence and quantity of analytes in the samples.

BACKGROUND OF THE INVENTION

Stool or fecal samples are routinely tested for the presence of parasites, fat, occult blood, viruses, bacteria and other organisms and chemicals in the diagnosis for various diseases. The stool is usually collected, placed in a clean container and processed for testing.

Stool collection is usually non-invasive and theoretically ideal for testing pediatric or geriatric patients, for testing away from a clinical site, for frequently repeated tests and for determining the presence of analytes which are likely to be found in the digestive tract. Stool can also be collected with a swab or finger cot during examination and applied directly to a test surface. For microscopic examination or occult blood testing, the sample can be spread directly on a test surface. For other tests, such as testing for fat, the stool may be suspended in a liquid medium such as water.

Traditional sample examinations have used complex chemical or microbiological procedures. These procedures are being rapidly replaced with immunoassay methods. Immunoassay techniques are highly sensitive and require only a small sample. Solid-phase techniques such as latex agglutination and enzyme immunoassays have been developed to such a stage of simplicity that they can be performed at home, at the doctor's office or other test sites without the need for highly trained laboratory technicians or expensive instruments. Application of solid-phase immunoassay procedures to the analysis of stool samples is thus highly desirable.

Application of immunoassay techniques to fecal analysis has proven to be difficult for several reasons. Stool handling is disagreeable and biohazardous, and sanitary and inoffensive procedures for processing stool have proven to be awkward and frequently complex. Analytes in stool samples are frequently unstable. Weighing, extracting and centrifuging, and storing samples are difficult except in a clinical laboratory equipped with suitable apparatus and skilled technicians.

Constituents of stool are known to interfere with solid-phase immunoassays. Immunoreactants immobilized on solid-phase are desorbed by stool constituents. Non-specific reactions occur. To increase the commercial use of immunoassay techniques for measuring analytes in stool, a number of problems must be solved. Instability of the analyte in the stool, interference from stool constituents, needs for extensive handling of the stool, equipment contamination, and instrumentation needs must be minimized. Simple preparation steps avoiding the use of expensive equipment and instruments are required to extend the use of immunoassay testing procedures to sites outside hospital and clinical laboratory environments.

DESCRIPTION OF THE PRIOR ART

Assay procedures including the preparation of concentrated suspensions of 10 and 25 wt.% stool in water or buffer solution have been described by Vellacott et al, *The Lancet* p 18 (Jan. 3, 1981) and Jilkunen et al, *Scand.J.Infec.D.* 17:245 (1985). These were centrifuged and sterile-filtered to provide a sample for testing.

Desorption of immunoreactants has been reduced by either heat treatment of the sample or by mixing 50 vol.% fetal calf serum or acid-protein buffer containing 5 vol.% bovine serum albumin (BSA) with the test sample.

Non-specificity problems have been overcome by heat-treating samples in the presence of a reducing agent.

Current stool handling procedures include storing and transporting stool samples in clean containers and reducing deterioration of analyte by maintaining the sample at low temperatures. Problems of non-uniformity are resolved by forming a suspension of an entire sample or by assaying several samples; the suspension is then treated by centrifugation, filtration, extraction and sterilization.

Current techniques for measuring hemoglobin in stool exemplify the problems. A widely used semi-quantitative procedure for measuring hemoglobin uses guaiac resin paper on which the stool is reacted with hydrogen peroxide. The reaction of hemoglobin with guaiac resin forms a blue color, the intensity of which is a function of the quantity of hemoglobin in the sample. This method does not distinguish hemoglobin derived from animal blood in food from human hemoglobin. Because this method is subject to variables derived from chemical and biochemical interference with the hemoglobin-guaiac resin reaction and variations in water content of the paper and stool, it is not truly quantitative.

A quantitative method for measuring hemoglobin in stool described in U.S. Pat. No. 4,378,971 involves heating a small amount of stool in a reducing acid milieu. Porphyrin, free from other contaminating fluorescent compounds, is extracted from the mixture. This procedure provides a very sensitive, quantitative measurement of hemoglobin in stool. However, it requires extensive handling, does not differentiate human and animal hemoglobins, and cannot be carried out rapidly.

The radialimmunodiffusion (RID) procedure described by Barrows, G.H. et al, *Am.J.CLin.Path.* 69:342-346 (1977) uses antibodies to human hemoglobin in conjunction with calibrators of known hemoglobin concentrations. A disk is punched out from filter paper, stool sample is applied to the disk, and the disk is placed on a RID plate. There it is allowed to react for 24 hours with a disk impregnated with the calibrators. This test has a detection limit of 0.3 mg of hemoglobin in 8 mg of stool. It requires overnight incubation. Use of filter paper limits sensitivity since all hemoglobin placed on the paper is not made available for the antigen-antibody reaction. Irreversible protein absorption may permit the release of as little as 5 to 10 percent of the hemoglobin placed on the paper.

U.S. Pat. No. 4,582,811 describes a procedure including binding hemoglobin in a sample with antibody impregnated in paper, and then reacting the product with a substrate to measure pseudoperoxidase activity of the hemoglobin.

U.S. Pat. No. 4,427,769 describes an immunological method involving extraction of hemoglobin applied to a guaiac resin coated paper, and measuring it with a sandwich enzyme immunoassay technique. Kim et al, *Clin.-Chim.Acta.* 152:175 (1985) describes a still further approach wherein a stool sample applied to a glass fiber filter is placed on a gel and allowed to incubate for 2-4 hours. Hemoglobin is quantitatively determined down to a limit of 0.2 mg of hemoglobin per gram of stool based on the presence or absence of a visible band.

The procedures describe above require the direct transfer of a stool specimen to the test system. Transfer of hemoglobin from the sample to the test system is only partial. Undesirable reactions caused by stool constituents are difficult to control with reagents due to their uniform distribution throughout the sample. Most of the procedures require a well equipped laboratory and trained technicians.

Adams and Layman, *Ann.Clin.Labs.Sci.* 4:343 (1974) describe a latex agglutination test involving blending 1 gm of stool in 100 ml of buffer solution and filtering the suspension. This test can detect hemoglobin down to a level of 10 ml of blood per gram of stool.

Vellacott, et al, *The Lancet.* 1:18 (1981) have described a fluorescent immunoassay method in which a 20% suspension of stool in water is used as a test sample. This sample is sonicated and centrifuged prior to testing.

Japanese Patent Application 60173471 (Dialog Derwent World Patent Acc. No. 85-259806/42) describes applying stool containing an analyte to a porous material. The porous material contains a carrier to which an antibody which binds with the analyte is attached. The sample is washed and contacted with further reagents to provide a change in spectroscopic characteristics.

European Patent Application 70366 (Dialog Derwent World Patent Acc. No. 83-12612K/06) describes an immunoperoxidase sandwich test method for determining hemoglobin, albumin or globulin in stool samples using beads upon which antibodies for the analyte are immobilized and a peroxidase labeled secondary antibody.

SUMMARY AND OBJECTS OF THE INVENTION

The method of this invention for preparing a fecal sample composition for immunoassay testing comprises forming a dispersion of 1 up to 10 wt.% and preferably from 1 to 5 wt.% of a stool sample in an aqueous fecal test solution. The aqueous fecal test solution can contain preservatives and endogenous interference reducing agents to protect the test sample components against assay related deterioration and the assay from interference. The aqueous fecal test solution of this invention contains at least one stool stabilizing agent or at least one analyte stabilizing agent. The aqueous fecal test solution also preferably contains agents which facilitate the immunoassay such as at least one inhibitor of endogenous enzymes which may interfere with the immunoassay and one or more non-immune animal proteins or polyamino acid polymers to reduce non-specific binding. Fecal solids in the dispersion are permitted to settle to form a clarified liquid phase substantially free from fecal solids. The clarified liquid phase is removed to provide a test sample free from fecal solids.

The preferred stool stabilizing agents include buffering agents, and antimicrobial agents such as antibacterial and/or antimycotic agents. The preferred analyte protecting agents include inhibitors of proteolytic, reductive and/or oxidative enzymes. For immunoassays using alkaline phosphatase enzyme labels, the preferred endogenous enzyme inhibitor inhibits the activity of endogenous alkaline phosphatase, such as formaldehyde or equally effective enzyme inhibitors.

The stool sample is preferably freshly collected or has been chilled to a temperature below $-20°$ C. immediately upon collection. Frozen stool is preferably then raised to a temperature within the range of from 2 to 6 C immediately before being dispersed in the aqueous fecal test solution.

The solid-phase immunoassay method of this invention for determining analyte in a fecal sample comprises contacting the clarified liquid phase with a solid support to which an anti-analyte is adhered for a time sufficient to permit antibody conjugation with analyte; and determining hemoglobin adhering to the insoluble support. For determining human hemoglobin in a sample of human stool according to this method, the aqueous fecal solution preferably contains an inhibiting amount of a proteinase inhibitor, from 0.02 to 0.5 wt.% of formaldehyde and from 0.01 to 10 wt.% of a non-immune animal protein.

It is an abject of this invention to provide an improved procedure for preparing stool samples for solid-phase immunoassay which is simple, quick and can be carried out in the home or other non-laboratory site by a technically unskilled person with simple, inexpensive resources. It is a further object of this invention to provide a procedure for preparing a stool sample composition which provides reduced interference with solid immunoassay procedures. A still further object of this invention is an improved immunoassay method for fecal occult blood testing of stool samples.

BRIEF DESCRIPTION OF THE DRAWINGS

FIG. 1 is a view of a sample preparation vial suitable for use in the method of this invention FIG. 2 is a cross-sectional view of the sample preparation vial of FIG. 1.

DETAILED DESCRIPTION OF THE INVENTION

This invention is a method for preparing a fecal or stool sample for analysis using immunological techniques. This procedure is described hereinafter in conjunction with an immunoassay procedure for determining human hemoglobin in a stool sample, by way of example, not by way of limitation. The sample preparation procedure described hereinbelow is equally suitable for preparing stool samples for determining other stool analytes by immunoassay methods, and the use of this procedure for all such applications is intended to be included within the scope of this invention.

In general, the method of this invention provides a stabilized stool sample solution which yields an improved result in immunoassays. The stool is suspended in an aqueous fecal test solution in a concentration of less than 10 wt.%. The fecal test solution contains agents which stabilize the stool and protect the analyte from deterioration. The solution also preferably contains agents which reduce endogenous sources of immunoassay interference and proteins to reduce non-specific binding. The clarified liquid from the stool suspension contains sufficient analyte for a highly accurate immunoassay determination. We have discovered that because the stool and analyte are diluted to low levels, the protective and inhibiting functions can be achieved with such low concentrations of reagents that the reagents do not significantly interfere with the immunoassay. Prior to this invention, effective stool stabilization and analyte protection with chemical or biochemical reagents was incompatible with immunoassay methods. The high reagent concentrations required greatly interfered with the immunoassays. Accordingly, expensive, time-consuming non-reagent purification and stabilization techniques were found necessary to prepare fecal samples for immunoassay analysis.

The method of this invention for preparing a fecal sample composition for immunoassay testing involves a first step of forming a dispersion of from 1 up to less than 10 wt.% and preferably from 1 to 5 wt.% of a stool sample in an aqueous fecal test solution. The aqueous fecal test solution of this invention contains at least one stool stabilizing agent and/or at least one analyte stabilizing agent. The aqueous fecal test solution also preferably contains agents which facilitate the immunoassay such as at least one inhibitor of endogenous enzymes which may interfere with the immunoassay and one or more non-immune animal protein or polyamino acid polymer to reduce non-specific binding.

For stabilizing the stool, the aqueous fecal test solution contains buffering agents and/or antimicrobial agents. The aqueous fecal test solution can be buffered to a pH selected to increase the stability of the stool. For hemoglobin immunoassays, a buffer solution having a pH of from 7.0 to 8.0 is desirable. Any conventional buffering agents can be used to prepare the test buffer solution, if they do not interfere with the later assay procedure and assay reagents. One example of a suitable buffering solution is standard phosphate buffered saline, pH 7.2 to 7.6 and preferably about 7.4.

The stool stabilizing agent can include any biocidal or biostatic agents which will inhibit microbial growth in the sample but will not interfere with the immunoassay. Any conventional biocidal or biostatic agent can be used which will not interfere with the later assay procedure and assay reagents. An example of suitable biocidal agents are antibiotics such as penicillin or streptomycin, and antimycotic agents such as fungizone. A commercial buffer solution containing these antimicrobial agents is available from Gibco Co., New York, NY. The concentration of the antibiotic and antimycotic agents is adjusted based on the activity of the reagent selected. In general, the level is sufficient to suppress the reproduction of the microbes and preferably is sufficient to kill a majority of them.

Particularly for proteinaceous analytes, the analyte stabilizing or protecting agent can be an inhibitor of enzyme activity which would affect the analyte. Inhibitors of proteolytic, reductive and oxidative enzymes are useful. Any conventional inhibitors of proteolytic, reductive or oxidative enzyme activity can be used to prepare the aqueous fecal test solution, if they do not interfere with the later assay procedure and assay reagents. Examples of suitable proteolytic activity inhibitors include phenylmethylsulfonylfluoride (PMSF), pepstatin A, Bestatin, and chymostatin (Sigma Chemical Co.). A suitable commercial product is the proteolytic activity inhibitor aprotinin, a derivative of bovine lung described by Kraut, H. et al, Z.Physiol.Chem. 198 97–101 (1930). The proteolytic activity inhibitor is present in a concentration sufficient to inhibit a major proportion of the proteolytic activity. Aprotinin can be present in concentrations of from 10,000 to 30,000 kallikrein inactivator units per liter of fecal test solution.

The aqueous fecal test solution also preferably contains reagents which inhibit or deactivate enzymatic activity which may interfere with the particular immunoassay procedure used. Particularly when the immunoassay uses alkaline phosphatase labeled reagents, endogenous alkaline phosphatase naturally present in the sample presents substantial interference. If alkaline phosphatase levels in the sample are not adequately suppressed by other reagents, the broadly active enzyme inhibitors or deactivators are useful. The preferred test system uses formaldehyde as an inhibitor of alkaline phosphatase in the sample. Other enzyme inhibitors include metal chelating agents, heavy metal ions, certain amino acids such as tyrosine and phenylalanine, and high concentrations of zinc or inorganic phosphates. Any conventional enzyme inhibitor can be used to prepare the aqueous fecal test solution, if it does not interfere with the later assay procedure and particularly any enzyme reactions used in the immunoassay procedure. The level of enzyme inhibitor or deactivator is selected to be sufficient to achieve the level of inhibition required for the sample. For the general stool samples, alkaline phosphatase inhibitors such as formaldehyde can be used in concentrations of from 0.01 to 0.5 wt.% and preferably in concentrations of from 0.01 to 0.2 wt.%.

A non-specific binding inhibitor is preferably present in the fecal test solution. Suitable non-specific binding inhibitors are non-immune water-soluble animal proteins and polyamino acids which would not interfere with the later assay procedure and particularly any protein measurements in the immunoassay procedure. Suitable animal proteins include bovine (BSA), human (HSA), rabbit (RSA), goat (GSA), sheep (SHA), and horse (HOSA) serum albumins, for example; serum gamma globulin, of the previously described animals and other animal proteins such as ovalbumin, fibrinogen, thrombin, transferin, glycoproteins, etc. Suitable water-soluble amino acid polymers include polylysine, polyglutamic acid, polyalanine, polyhistidine, polymethionine, polyproline, and the like. For assays where non-specific binding presents a problem, the concentration of the non-specific binding inhibitor can be from 0.1 to 1.0 wt.% and is preferably from 1 to 5 wt.%.

The preserved aqueous fecal test solution can also contain other protective agents including proteins, carbohydrates, salts and the like which provide a protective function.

Microbial and chemical changes in the sample should be inhibited and preferably completely arrested immediately after the sample is obtained. The stool is preferably dispersed in the aqueous fecal test solution immediately after being obtained, where the preservatives and other reagents in the buffer solution will stabilize the sample. If the stool is to be stored or shipped before testing, it should be quickly frozen to a temperature below −20° C. immediately after being obtained to prevent chemical and microbial changes, and the sample should be maintained at this temperature until the sample is to be dispersed in the aqueous fecal test solution. Immediately before being dispersed, the frozen sample temperature is raised to a temperature within the range of from 2 to 6 C.

The fecal solids in the dispersion are then permitted to settle to form a liquid phase substantially free from fecal solids and the clarified liquid phase is removed, providing a test sample substantially free from fecal solids.

FIG. 1 shows an open vial and spatula combination which is suitable for treating the stool samples according to this invention, and FIG. 2 is a cross-sectional representation thereof. The container 2 has a body 4 made of transparent organic polymer or glass with level or volume graduation lines 6 on the outer surface thereof. The bottom of the body is formed into a conical solids receptor 8, enclosed within a cylindrical stand 10 which maintains the body 4 in an axially upright position. The cap 12 is threaded to form a sealed, threaded engagement with the body threads 14. A spatula-stirrer 16 having a flattened end 18 is mounted in the cap 12, extending downward into the dispersion and settling cavity 20 formed by the body 4.

The spatula or sample spoon 16 is dimensioned to take a selected amount of stool and disperse it in a selected volume of liquid 22 in the vial 2. The suspension is permitted to settle, and the solids are collected in the conical bottom 8, leaving a clarified liquid in the upper portion of the container. This container is suitable for preparing dilutions of stool for qualitative immunoassays.

A further dilution can be made by transferring clarified liquid from the vial to another container of fecal test solution or another suitable aqueous fecal test dilution medium. For competition immunoassays, the fecal test solution or dilution medium can be used for obtaining the desired dilutions. For sandwich immunoassays, the fecal test solution or dilution medium can contain suitable reducing agents as required for the analyte determinations.

Containers of the type shown in FIG. 1 and FIG. 2 are also suitable for storage and shipment of stool samples dispersed in the fecal test solution. With dilution in an inhibitory buffer solution, the odor is minimized and the appearance of the sample made less objectionable. However, in the preferred method, the fresh stool is transferred into liquid medium in the container for clarification and testing.

Surprisingly, the sample preparation procedure of this invention, when carried out with suitable reagent inhibitors in the fecal test solution, reduces interfering activities far more efficiently than the prior art methods and without their complicated, lengthy and elaborate procedures. The dispersion of sample in the buffer solution allows a uniform and rapid inhibitory and protective action by the reagents. The arrest of the potential harmful effects of the stool constituents in the subsequent immunoassay is more efficient and complete than with the prior art procedures.

A solid-phase immunoassay for determining an analyte in a human stool sample according to this invention comprises the steps of contacting the clarified liquid test sample with a solid support to which an anti-analyte antibody is adhered for a time sufficient to permit antibody conjugation with analyte, and determining analyte adhering to the insoluble support. The choice of aqueous buffer solution inhibitors and reagents is selected to facilitate the immunoassay procedure to be carried out. A wide variety of solid-phase immunoassay procedures including latex agglutination, competition and sandwich immunoassays can be carried out with a sample prepared according to this invention. These procedures can use antibodies or reagent analytes labeled with a wide variety of physically detectable labels or with active labels such as enzymes or enzyme substrates which upon a further reaction yield physically detectable labels.

By way of example, the clarified liquid can be used for determining human hemoglobin in the sample using an anti-(human hemoglobin) antibody. For this procedure the fecal test solution preferably contains as stool stabilizing agents, buffers and antimicrobial agents; and as an analyte protecting agent, a proteolytic enzyme inhibitor. For immunoassays using a phosphatase labeled reagent, the aqueous fecal test solution preferably also contains a reducing agent and a non-specific binding inhibitor. A aqueous fecal test solution for this assay preferably is buffered to a pH of from 7.0 to 8.0, and contains a biocidal amount of an antimicrobial agent, an inhibiting amount of a proteinase inhibitor, from 0.02 to 0.5 wt.% and optimally from 0.02 to 0.1 wt.% of formaldehyde, and from 1 to 10 wt.% of an animal albumin.

This invention is further illustrated by the following specific, but non-limiting examples. Temperatures are given in degrees Centigrade and percents as weight percents unless otherwise specified. Examples which are constructively reduced to practice herein are presented in the present tense, and examples representing laboratory experiments previously reduced to practice are presented in the past tense.

EXAMPLE 1

Fecal Occult Blood Immunoassay

Goats are immunized by standard procedures with purified human hemoglobin Variance A (Isolab PH 100, Akron, OH). Bleeds from the goats are tested against human hemoglobin until the presence of antibodies to hemoglobin are confirmed. Polystyrene macrobeads (6-8 mm) are suspended in the anti-serum diluted in glycine-saline buffer, pH 8.2 to provide a coating of the goat anti-(human hemoglobin) antibody.

Dialyzed calf-intestine alkaline phosphatase is mixed with hemoglobin in the presence of gluteraldehyde to form a hemoglobin-alkaline phosphatase conjugate. The reaction product is purified on a SEPHACYL S-300 column (Pharmacia), eluting with tris buffer containing $MgCl_2$.

The buffered aqueous fecal test solution is 0.02 M phosphate buffered saline, pH 7.4, containing 0.1 wt.% sodium azide, 1 wt.% bovine serum albumin, 10,000 u/L aprotinin (TRASYLOL, Mobay Chemical, New York, NY) and 694 microliters/liter of formaldehyde.

A stool sample (1 gm) is dispersed in 30 ml of the fecal test solution.

Hemoglobin calibrator controls are made by dissolving human hemoglobin in desired concentrations in the testing buffer solution.

The enzyme substrate p-nitrophenyl phosphate (SIGMA 104 phosphatase substrate tablets, Sigma Chemical Company, St. Louis, MO) is dissolved in a buffer which contains 0.05 M $NaHCO_3$, 0.05 M NaCl and 0.1 mM $MgCl_2$. The tablet must be completely dissolved.

Assay Procedure

1. Allow all assay reagents and specimens to equilibrate to room temperature.

2. Label test tubes in duplicate for each calibrator, control and sample.
3. Pipette 50 microliters each of calibrator, control and clarified stool sample solution into the bottom of each tube. The volume can be selected from the range of from 10 to 100 microliters.
4. Pipette 1 ml of the buffer solution into each tube, shaking the tubes to mix.
5. Place the required number of beads onto absorbent paper and drop one bead into each tube. Shake to mix the bead and liquid.
6. Incubate all tubes at rm temp for 30 min. During each incubation, shake tubes 3 to 4 times at regular intervals with sufficient force to lift the bead off the tube bottom.
7. Decant or aspirate liquid from all tubes. Wash each bead with 5 ml of distilled water at rm temp. Decant or aspirate liquid from all tubes.
8 Repeat washing step (7) two more times, and after the last wash, remove all residual water with an aspirator or invert the tubes over absorbent paper.
9. Add 200 microliters of prepared hemoglobin-alkaline phosphatase conjugate solution to all tubes, and incubate all tubes at rm temp for 30 min. Shake tubes 3 to 4 times at regular intervals during incubation. The incubation times for each tube must be the same. This can be accomplished by pipetting all reagents into all tubes in the same order without interruptions and in the same elapsed time interval.
10. Wash each bead with 5 ml of distilled water at rm temp. Decant or aspirate liquid from each tube.
11. Repeat the washing step (10) two more times. After the last wash, remove all residual water with an aspirator or invert tubes over absorbent paper.
12. Dispense 200 microliters of enzyme substrate solution into each tube, and incubate each tube for 30 min in a dark plate at rm temp. Shake tubes 3 to 4 times at regular intervals during incubation. The incubation times for each tube must be the same. The pipetting procedure in step (9) is suggested to accomplish this.
13. Read absorbance at 405 nm.

The average absorbance is calculated for the calibrators, controls and samples. The data obtained from the calibrators are plotted on semi-log graph paper, plotting the absorbance on the Y-axis and hemoglobin concentration on the X-axis. A best fitting curve is drawn along the points to provide a calibration curve.

Applying the sample absorbance to the curve, the sample concentration is determined.

The above procedure was carried out with a calibrator control series: a positive control formed by mixing human hemoglobin in the buffer solution, and a negative control of rabbit hemoglobin in buffer solution. The results are summarized in Table A.

TABLE A

| Calibrators | Concentration (microgm/ml) | O.D. (405 nm) | Average O.D. (405 nm) |
|---|---|---|---|
| A | 0 | 1.526 | |
| | | 1.569 | 1.547 |
| B | 1 | 1.420 | |
| | | 1.400 | 1.410 |
| C | 5 | 0.945 | |
| | | 1.006 | 0.976 |
| D | 25 | 0.381 | |
| | | 0.410 | 0.395 |
| E | 50 | 0.330 | |
| Positive Control | 5 | 1.034 | |
| | | 1.049 | 1.041 |

TABLE A-continued

| Calibrators | Concentration (microgm/ml) | O.D. (405 nm) | Average O.D. (405 nm) |
|---|---|---|---|
| Negative Control | 0.2 | 1.558 | |
| | | 1.422 | 1.500 |

$$\text{mg hemoglobin/gm stool} = \frac{\text{microgm/ml hemoglobin} \cdot 30}{\text{stool wt. (mg)}}$$

EXAMPLE 2

Alkaline Phosphatase Inhibition

Eight stool suspensions to which no inhibitors to endogenous alkaline phosphatase were added were tested according to the procedure described in Example 1. The same samples were suspended in fecal test solution in various dilutions and tested according to the procedure of Example 1. The Calibrators containing no human hemoglobin were also tested. The results obtained are shown in Table B.

TABLE B

| Stool Sample | O.D. Ratio | | | |
|---|---|---|---|---|
| | 0% $CH_2O$ | 4% $CH_2O$ | 1% $CH_2O$ | 0.5% $CH_2O$ |
| 1 | 2.7 | .72 | .93 | 2.0 |
| 2 | 2.6 | .76 | .86 | 1.6 |
| 3 | 1.8 | .43 | .60 | 1.0 |
| 4 | 1.3 | .52 | .73 | 0.8 |
| 5 | 0.9 | .47 | .49 | 0.9 |
| 6 | 1.3 | .46 | .74 | 0.9 |
| 7 | 0.8 | .52 | .66 | 0.9 |
| 8 | 2.2 | .54 | .94 | 1.0 |

$$\text{Ratio of O.D.} = \frac{\text{O.D. of Sample Suspension}}{\text{O.D. of Calibrators}}$$

An O.D. Ratio of 1.0 represents optimum inhibition. The data demonstrates that an optimum inhibition is achieved with most samples at a formaldehyde concentration of less than 1.0 wt.% and in several samples, an optimum inhibition is achieved with a formaldehyde concentration of 0.5 wt.% formaldehyde.

EXAMPLE 3

Analyte Stabilization

This example demonstrates that hemoglobin is unstable in undiluted stool, that the addition of stabilizer to the undiluted stool is ineffective as a stabilizing effort, and that with stool diluted according to this invention in a fecal test liquid, hemoglobin content can be stabilized at room temperature.

Procedure A: 300 Micrograms of human hemoglobin was added to 0.1 gm of undiluted stool, and the mixture was permitted to stand for 10 min at rm temp. The stool was then suspended in 30 ml of fecal test solution, and the concentration of hemoglobin was measured according to the procedure of Example 1. A mean measured concentration of hemoglobin of 2.6 microgm/ml was found compared with an expected 10 microgm/ml.

Procedure B: Procedure A was repeated except that 20 microliters of aprotinin stabilizer was added to the undiluted stool at the same time as the 300 microgm of hemoglobin. The mean measured concentration of hemoglobin was found to be 0.16 microgm/ml compared with the expected 10 microgm/ml, demonstrating that the stabilizer was not effective for protecting hemoglobin when added to the undiluted stool.

Procedure C: Procedure B was repeated except that 3.33 mg/ml of stool was suspended in fecal test solution containing aprotinin before the hemoglobin was added.

The mean measured concentration of hemoglobin was found to be 10 microgm/ml, the expected concentration, demonstrating that by diluting the stool sample according to this invention, effective stabilization of hemoglobin can be achieved.

EXAMPLE 4

Hemoglobin Recovery

This example demonstrates that a major proportion of hemoglobin applied to a filter paper surface cannot be recovered, in contrast to a high recovery level in a dilute suspension.

A 500 mg sample of stool was mixed with 1.0 ml of fecal test solution described in Example 1. A uniformly mixed portion of this sample was placed on a filter paper membrane. The weight of the sample was determined by weighting the membrane before and after application of the sample. The membrane was then placed in 1.0 ml of the fecal test solution and allowed to stand for 15 to 180 min. A sample of this buffer was assayed according to the procedure of Example 1. The procedure was repeated except that the sample was added directly to fecal test liquid. The hemoglobin recoveries are shown in Table C:

TABLE C

| Extraction Time, min | Recovery from Filter Paper, % | Recovery from Suspension, % |
|---|---|---|
| 15 | 2.4 | 70.8 |
| 30 | 3.6 | 59.2 |
| 60 | 2.3 | 107.7 |
| 120 | 2.4 | 101.2 |
| 180 | 2.8 | 33.1 |

Substantially higher hemoglobin recoveries were obtained when the sample was placed directly in the fecal test solution.

EXAMPLE 5

Stool Dilution

Added Hemoglobin Recovery

This example demonstrates the increase in hemoglobin recovery achieved by diluting the stool in the fecal test solution described in Example 1. A sample of stool containing 25 wt.% stool and 75 microgm/ml of hemoglobin in fecal test solution, and the suspension is diluted in fecal test solution in a series of dilutions. The hemoglobin concentration of the diluted solutions were measured according to the procedure of Example 1, and the percentages of hemoglobin, compared to the theoretical amounts of hemoglobin available for recovery were determined. The results are shown in Table D:

TABLE D

| Dilution, (v/v) | Measured Hemoglogin, % |
|---|---|
| None | 37.3 |
| 1:2 | 61.3 |
| 1:4 | 68.4 |
| 1:8 | 100 |
| 1:16 | 100 |
| 1:32 | 100 |

The data show that recovery is poor in concentrated stool suspensions, and recovery is higher when the stool is diluted to concentrations of 3 wt.% or less.

EXAMPLE 6

Stool Dilution

Added Hemoglobin Recovery

This example demonstrates the comparative increase in hemoglobin recovery achieved by diluting stool mixed with 10 microgm/ml of hemoglobin in the fecal test solution of Example 1 to concentrations of 3 wt.% and 10 wt.% stool. The hemoglobin was measured according to the procedure of Example 1. The results are shown in Table E.

TABLE E

| Stool Sample | Recovery, microgm/ml | |
|---|---|---|
| | 3% Stool | 10% Stool |
| 1 | 11.85 | 9.1 |
| 2 | 11.86 | 11.3 |
| 3 | 11.40 | 8.3 |
| 4 | 10.3 | 11.8 |
| 5 | 12.9 | 8.1 |
| 6 | 9.9 | 10.4 |
| 7 | 10.7 | 9.4 |
| 8 | 10.7 | 10.0 |
| 9 | 11.5 | 11.4 |
| 10 | 12.1 | 9.0 |
| 11 | 9.9 | 13.8 |
| 12 | 9.1 | 5.4 |

This data shows reduction in hemoglobin recovery varies from stool to stool, and that in general, a dilution of 10% stool gave lower recoveries than the lower dilution to 3%.

EXAMPLE 7

Stool Dilution

Endogenous Hemoglobin Recovery

This example demonstrates the comparative increase in endogenous hemoglobin recovery achieved by diluting stool containing endogenous hemoglobin in the fecal test solution of Example 1 to concentrations of 3 wt.% and 10 wt.% stool. The hemoglobin was measured according to the procedure of Example 1. A Measured Ratio was calculated with the formula:

$$\text{Measured ratio} = \frac{\text{O.D. with 10\% dilution}}{3.33 \times \text{O.D. with 3\% dilution}}$$

The results are shown in Table F.

TABLE F

| Stool Sample | Recovery, μgm/ml | | Measured Ratio |
|---|---|---|---|
| | 3% Stool | 10% Stool | |
| 1 | 9.3 | 18.0 | 64.3 |
| 2 | 9.5 | 18.7 | 65.7 |
| 3 | 11.4 | 9.8 | 28.7 |
| 4 | 9.2 | 5.4 | 19.6 |

This example again shows that hemoglobin recovery is increased by diluting the stool sample, and that the results obtained with endogenous hemoglobin correlated well with samples wherein the hemoglobin is added to the sample.

EXAMPLE 8

Enzyme Inhibition

Endogenous Hemoglobin Measurement

Portions of the stool samples used in Example 7 were diluted in 3 wt.% and 10 wt.% concentrations in the fecal test solution of Example 1 containing 10,000 u/L aprotinin and 0.026 wt.% formaldehyde, Inhibitor Conc. A. Another set of portions of the stool samples used in Example 7 were diluted in 3 wt.% and 10 wt.% concentrations in the fecal test solution containing 30,000 u/L aprotinin and 0.078 wt.% formaldehyde, Inhibitor Conc. B, three times the former concentration of both enzyme inhibitors. The hemoglobin concentrations of all samples were then measured according to the procedure of Example 1, and the Measured Ratio of the hemoglobin concentrations for each stool sample with each inhibitor concentration was calculated according to the formula in Example 7. The results are shown in Table G.

TABLE G

| Stool Sample | Hemoglobin Recovery | |
|---|---|---|
| | Measured Ratio Inhibitor Conc. A | Measured Ratio Inhibitor Conc. B |
| 1 | 64.3 | 96.3 |
| 2 | 65.7 | 71.0 |
| 3 | 28.7 | 30.2 |
| 4 | 19.6 | 24.0 |

This example shows that the loss in hemoglobin recovery and measurement experienced when the stool suspension is more concentrated can be partially compensated by increasing the inhibitor concentrations. However, the higher inhibitor concentrations interfere with the measurement of the hemoglobin values and flatten the response curve. By using more dilute suspensions, good recovery and measurement can be made with far smaller amounts of inhibitor, substantially reducing inhibitor interference with the assay.

EXAMPLE 9

Correlation with $^{51}$Cr

Isolabeled Erythrocytes

Stool samples were obtained from 163 patients who had ingested $^{51}$Cr isolabeled red blood cells as part of a blood loss test. The measurement of $^{51}$Cr is an absolute method which is used as a reference for determining accuracy of hemoglobin assays in stool. The hemoglobin in the stool was also measured by the procedure of Example 1 with 0.18 wt.% and 6.6 wt.% concentrations of stool in fecal test solutions. The results obtained with the method of the invention (IMMUNOCCULT ®) Test) were correlated with the blood loss determined by Geiger counter measurement of the $^{51}$Cr in the stool. The following relationship was established between the two assays:

$$I = (0.72 \times C) + 0.07$$

wherein

I is the ml of blood loss by the method of this invention; and

C is the ml of blood loss by $^{51}$Cr measurement.

The regression coefficient was 0.84, demonstrating an acceptable quantitative relationship between the method of this invention and the reference method.

EXAMPLE 10

Semi-Quantitative Method

One part by weight of a series of stool samples were suspended in more than 10 parts of the fecal test liquid described in Example 1. 10 Microliter (10 μl) and 50 microliter (50 μl) portions of the clarified suspension were measured by the procedure of Example 1, the IMMUNOCCULT ® Test. The samples were also measured for the quantitative estimate of hemoglobin by the HEMOCCULT ® Test. A comparison of the results are shown in Table H.

TABLE H

| Stool Sample | HEMOCCULT Test | IMMUNOCCULT ® Test, ug/ml | | |
|---|---|---|---|---|
| | | 10 μl | 50 μl | Ratio |
| 1 | 3+ | 4.1 | 22.5 | 5.5 |
| 2 | 2+ | 4.4 | 21.0 | 4.7 |
| 3 | 4+ | 65.2 | 203.0 | 3.1 |
| 4 | 3+ | 17.0 | 23.7 | 1.4 |
| 5 | 1+ | 0.1 | 0.1 | 1.0 |
| 6 | 1+ | 0.1 | 1.3 | 13.0 |
| 7 | −ve | 0.75 | 0.72 | 1.0 |
| 8 | −ve | 1.01 | 0.97 | 1.0 |
| 9 | −ve | 0.05 | 0.05 | 1.0 |
| 10 | −ve | 0.47 | 2.47 | 4.5 |
| 11 | −ve | 1.08 | 1.28 | 1.2 |
| 12 | −ve | 1.89 | 1.46 | 0.8 |
| 13 | −ve | 1.38 | 2.29 | 1.7 |
| 14 | −ve | 1.91 | 1.29 | 0.7 |
| 15 | −ve | 0.26 | 0.02 | 0.1 |
| 16 | −ve | 0.20 | 0.08 | 0.4 |
| 17 | | 0.01 | 0.42 | 42.0 |

In the table, "ve" stands for value

As can be seen comparing the results in Table H, the ratios of the absolute values 10 μl/50 μl is high for the +ve HEMOCCULT Test samples. In some samples, the values are low and the ratio is also low, indicating a true value sample. In other samples, the values are low but the ratios are high, indicating true borderline patients with some blood loss. As shown by the comparison, the HEMOCCULT Test may indicate a −value or a ± value for low hemoglobin samples when the IMMUNOCCULT ® Test provides a clearly positive indication of blood loss. IMMUNOCCULT ® and HEMOCCULT are registered trademarks.

EXAMPLE 11

Comparison to Guaiac Paper Assay

A comparison of results of assays using guaiac paper and using two assays according to the present invention. The first assay according to this invention was performed using the procedure of Example 1, the IMMUNOCCULT ® EIA Test. The second assay was performed using the procedure described below, the IMMUNOCCULT ® LXI Test.

The buffered aqueous test solution is the same as in Example 1.

The anti-(human hemoglobin) antibody was prepared as described in Example 1. The antibody was diluted in phosphate buffered saline pH 7.4 for use in this assay.

The latex particles are prepared by binding human hemoglobin (Sigma Chemical Co., St. Louis, MO) to carboxylated latex (Seradyne Corporation, Indianapolis, IN) according to the manufacturer's directions.

The assay was performed as described below.

Assay Procedure

1. Allow all assay reagents and specimens to equilibrate to room temperature.
2. Label test tubes in duplicate for each calibrator, control and sample.
3. Pipette 30 microliters (or one drop) of each of calibrator, control and clarified stool sample solution into each well of an agglutination slide (preferably, a 6.25" × 6.25' agglutination slide with a black background and blue rings available commercially from Scientific Products (McGaw Park, IL).
4. Pipette 30 microliters (or one drop) of antibody solution into each well.
5. Pipette 30 microliters (or one drop) of the latex particle solution into each well. Mix thoroughly using the dispensing-stirring devices provided with the kit.
6. Place slides on a rotator. Observe negative control agglutination which should occur in 3 to 7 minutes. Observe agglutination of test sample and positive and negative controls. The test results are expressed as + (no agglutination), − (agglutination) or ± (equivocal).

The samples for each immunoassay were a 3% suspension in test solution.

The COLOSCREEN III VPI kit (Helena Laboratories, Beaumont, TX) was used to perform the guaiac paper test. The test was performed according to the manufacturer's directions.

Samples from 41 patients with at least two serial stool specimens were tested by the guaiac paper test. Suspensions of these specimens were frozen and shipped for immunoassay testing. The results of the tests are illustrated in Table I.

TABLE I

| Assay | Results | | | | | | |
|---|---|---|---|---|---|---|---|
| COLOSCREEN III VPI | − | + | − | + | + | − | − |
| IMMUNOCCULT ®-LXI | − | + | +[1] | +[2] | − | + | − |
| IMMUNOCCULT ® EIA | − | + | + | − | − | − | + |
| Number of Patients | 25 | 6 | 4 | 3 | 1 | 1 | 1 |

[1]The results of the assay of one patient sample were equivocal.
[2]The results of the assay of two patient samples were equivocal.

Agreement between the guaiac test and the immunoassays was 76%. This finding is consistent with literature reports of the results with other immunoassays of stool samples prepared by other methods. In particular, Songster et al, Immunochemical Detection of *Human Fecal Occult Blood* In: Correctal Cancer: Prevention, Epidemiology and Screening Winawar et al eds. New York Raven (1980) p.193-204 and Vaananen et al Clin.-Chem. 34(a):1763-1766 (1988) discuss the comparison of guaiac paper and immunological assays of fecal occult blood.

Thus, the assay method of this invention is useful in confirming guaiac paper tests, particularly when the patients are not following the recommended dietary restrictions regarding eating meat.

We claim:

1. A solid-phase immunoassay for determining hemoglobin in a human stool samples comprising in a process for detecting hemoglobin the steps of
   (a) forming a dispersion of from 1 up to less than 10 wt.% of a stool sample in an aqueous fecal test solution containing a buffer, a biocide in a concentration for inhibiting microbial growth and a proteolytic enzyme inhibitor in a concentration sufficient to inactivate a major proportion of the proteolytic activity;
   (b) permitting the fecal solids in the dispersion to settle to form a liquid phase substantially free from fecal solids;
   (c) removing the liquid phase to provide a test sample substantially free from fecal solids;
   (d) contacting the liquid test sample with a solid support to which an anti-(human hemoglobin) antibody is adhered for a time sufficient to permit antibody conjugation with analyte; and
   (e) determining analyte adhering to the insoluble support.

2. The method of claim 1 wherein the stool sample has been freshly collected.

3. The method of claim 1, wherein the stool sample dispersed in the aqueous fecal test solution has been preserved by reducing the stool sample temperature to less than −20° C. while fresh, maintaining the stool sample at a temperature of less than −20° C. until test sample preparation, and the test sample preparation comprises raising the stool sample temperature up to a temperature of from 2 to 6° C. before dispersing the stool sample in the aqueous fecal test solution.

4. The solid-phase immunoassay method of claim 1 wherein the aqueous fecal test solution additionally contains a nonimmune animal protein in a concentration sufficient to inhibit non-specific binding.

5. The solid-phase immunoassay method of claim 4 wherein the non-immune animal protein comprises from 0.01 to 10 wt.% of an animal albumin.

6. The method of claim 1 wherein said immunoassay involves the use of alkaline phosphatase and said aqueous fecal test solution additionally contains an endogenous alkaline phosphatase inhibitor in an amount sufficient to inhibit endogenous alkaline phosphatase activity.

7. The method of claim 6 wherein the endogenous alkaline phosphatase inhibitor is from 0.01 to 0.5 wt.% formaldehyde.

8. A method for preparing a stabilized stool sample solution for immunoassay testing comprising the steps of
   (a) forming a dispersion of from 1 up to less than 10 wt.% of a stool sample in an aqueous fecal test solution containing:
      (i) a buffer;
      (ii) a biocidal or biostatic compound in a concentration sufficient for inhibiting microbial growth;
      (iii) from 10,000 to 30,000 kallikrein inactivator u/L of aprotinin;
      (iv) from 0.01 to 0.5 wt.% formaldehyde; and
      (v) a non-immune animal protein in a concentration sufficient to inhibit non-specific binding;
   wherein the stool sample is freshly collected or was frozen upon collection;
   (b) permitting the fecal solids in the dispersion to settle to form a liquid phase substantially free from fecal solids; and
   (c) removing the liquid phase to provide a test sample substantially free from fecal solids.

* * * * *